US012788318B1

(12) United States Patent
Alomri et al.

(10) Patent No.: US 12,788,318 B1
(45) Date of Patent: Nov. 10, 2026

(54) SYSTEMS AND DEVICES FOR PHYSIOLOGICAL AROUSAL MANAGEMENT

(71) Applicant: University of Jeddah, Jeddah (SA)

(72) Inventors: Ridwan Musbeh Alomri, Jeddah (SA); Yousef S. Alsahafi, Jeddah (SA)

(73) Assignee: University of Jeddah, Jeddah (SA)

( * ) Notice: Subject to any disclaimer, the term of this patent is extended or adjusted under 35 U.S.C. 154(b) by 0 days.

(21) Appl. No.: 19/345,491

(22) Filed: Sep. 30, 2025

(51) Int. Cl.

| | |
|---|---|
| ***A61B 5/00*** | (2006.01) |
| ***A61B 5/02*** | (2006.01) |
| ***A61B 5/0205*** | (2006.01) |
| ***A61B 5/024*** | (2006.01) |
| ***A61B 5/026*** | (2006.01) |
| ***A61B 5/08*** | (2006.01) |

(52) U.S. Cl.

CPC .......... *A61B 5/486* (2013.01); *A61B 5/02028* (2013.01); *A61B 5/0205* (2013.01); *A61B 5/02427* (2013.01); *A61B 5/0261* (2013.01); *A61B 5/0803* (2013.01); *A61B 5/0816* (2013.01); *A61B 5/4035* (2013.01); *A61B 5/6826* (2013.01); *A61B 5/7203* (2013.01); *A61B 5/7264* (2013.01); *A61B 5/7405* (2013.01); *A61B 5/742* (2013.01); *A61B 5/7455* (2013.01); *A61B 5/746* (2013.01); *A61B 5/7475* (2013.01); *A61B 2560/0209* (2013.01); *A61B 2560/0462* (2013.01)

(58) Field of Classification Search
None
See application file for complete search history.

(56) References Cited

U.S. PATENT DOCUMENTS

| | | | | |
|---|---|---|---|---|
| 6,081,742 | A * | 6/2000 | Amano | A61B 5/0205 600/513 |
| 9,872,968 | B2 | 1/2018 | De Zambotti et al. | |
| 2006/0217615 | A1* | 9/2006 | Huiku | A61B 5/4821 600/484 |
| 2017/0209055 | A1* | 7/2017 | Pantelopoulos | A61B 5/7203 |
| 2019/0150761 | A1* | 5/2019 | Sandgaard | A61B 5/02042 |
| 2024/0298919 | A1* | 9/2024 | Vallat | A61B 5/7435 |

* cited by examiner

*Primary Examiner* — Ankit D Tejani
(74) *Attorney, Agent, or Firm* — Pabst Patent Group LLP

(57) ABSTRACT

Described herein is an interactive biofeedback therapy designed to aid individuals with insomnia, especially those experiencing difficulty initiating sleep due to cognitive hyperarousal and physiological activation. The system contains a wearable ring device that monitors Pulse Wave Amplitude (PWA)—a biomarker indicative of sympathetic nervous system overactivity. The ring device, in conjunction with a processing unit, for example a smartphone application, collects PWA data to calculate and track PWA drops, signaling physiological arousal. When PWA drops beyond a defined threshold, the device issues real-time feedback, prompting the subject to engage in relaxation techniques.

19 Claims, 6 Drawing Sheets

SYSTEMS AND DEVICES FOR PHYSIOLOGICAL AROUSAL MANAGEMENT

FIELD OF THE INVENTION

The invention is generally in the field of devices, particularly a wearable device containing a sensor and operably linked to a processor, for monitoring physiological data and detecting pulse wave amplitude drops for managing one or more diseases or disorders associated with a subject's sympathetic nervous system through real-time biofeedback.

BACKGROUND OF THE INVENTION

Insomnia, a prevalent sleep disorder, is characterized by difficulties in initiating, maintaining sleep and/or awakening prematurely, leading to significant daytime dysfunction and impaired quality of life. Researchers have found that up to 43% of the general population have reported at least one of these symptoms. Patients typically also report related issues such as daytime dysfunction, including fatigue, daytime sleepiness, impairment in cognitive performance, and mood disturbances that adversely affect quality of life. More specifically, sleep-onset latency is one of the common insomnia types and is distinguished by high levels of cognitive activity, worry, rumination, and negative thoughts together with over-autonomic activation. Insomnia affects approximately 10-30% of the global population, with chronic insomnia impacting up to 15%. In the United States alone, insomnia results in an estimated annual economic cost exceeding $100 billion due to lost productivity, healthcare expenses, and accident-related costs. Studies have shown that individuals with chronic insomnia are three times more likely to experience depression and anxiety disorders. Additionally, insomnia is linked to an increased risk of cardiovascular diseases, obesity, and impaired immune function. These statistics underscore the urgent need for effective interventions that can alleviate the widespread and multifaceted impacts of insomnia.

Traditional treatments for insomnia, such as pharmacological interventions and Cognitive-Behavioral Therapy for Insomnia (CBT-I), offer varying degrees of efficacy but are often limited by side effects, accessibility, and long-term sustainability. As the demand for effective and non-invasive sleep therapies grows, innovative solutions that leverage modern technology to address the multifaceted nature of insomnia are increasingly essential. Therefore, effective management of insomnia is highly needed for enhancing overall health and well-being. Chronic insomnia is also associated with a heightened risk of developing mental health disorders, cardiovascular diseases, and impaired cognitive functions. Moreover, the economic impact of insomnia includes increased healthcare costs, reduced workplace productivity, and heightened risk of accidents. Addressing insomnia through advanced therapeutic technologies can mitigate these adverse outcomes, improve individuals' quality of life, and reduce the societal and economic burdens associated with sleep disorders. Therefore, developing innovative, accessible, and cost-effective treatments is of paramount importance in the field of sleep medicine.

Several approaches have been developed to address insomnia, including pharmacological treatments, CBT-I, and various biofeedback and wearable technologies. Pharmacological solutions, while effective in the short term, often lead to dependency and rebound insomnia upon discontinuation. CBT-I, a non-pharmacological approach, has shown long-term efficacy but is limited by accessibility and the need for trained therapists. In the realm of biofeedback, devices like the Virtual Reality Sleep Assistant (VRSA) have been introduced to provide immersive environments that help reduce arousal and promote sleep. For example, U.S. Pat. No. 9,872,968 discloses a Virtual Reality Sleep Assistant (VRSA) biofeedback device, which uses both visual and auditory inputs and many biomarkers. However, these systems often involve high costs and complex setups, limiting their widespread adoption. Additionally, existing biofeedback devices typically operate under daytime supervision, failing to provide real-time intervention during actual episodes of insomnia. Consequently, there is a need for low-cost biofeedback therapy treatment that can enable an individual suffering with insomnia to interactively and independently monitor themselves and apply standard biofeedback techniques to control physiological and cognitive arousals at home.

Given that insomnia is characterized by hyperactivity in the cognitive and physiological domains, biofeedback therapy for insomnia has tremendous application as a treatment option, particularly for sleep onset latency. However, it does possess certain limitations, the most critical of which is that established biofeedback therapies are typically administered only under the supervision of a specialist, typically during daytime hours, where subjects are taught how to control the symptom of physiological arousal. This is a drawback since the program is being applied outside of the actual occurrence of the condition. Likewise, insomniacs report the symptom of having a racing or hyperactive mind, where they are unable to stop thinking about stressors or other matters at nighttime. Addressing this symptom is important to the treatment of insomnia; but treatment of hyperactive mind is not a component of available biofeedback therapy systems.

In sum, despite advancements in insomnia treatments, significant gaps remain in providing accessible, cost-effective, and real-time solutions that can be utilized autonomously by individuals during nighttime arousal episodes. Current biofeedback therapies require specialist supervision and are confined to daytime use, making them ineffective during the actual moments of insomnia. Furthermore, high-cost solutions like virtual reality-based systems are not feasible for the average consumer, restricting their availability from a broader population. Accordingly, there is a clear need for a low-cost, user-friendly biofeedback system that can deliver immediate interventions at any time as needed, including during sleep disturbances, helping users manage both physiological and cognitive arousals without the necessity of clinical settings or expensive equipment.

Therefore, it is an object of the invention to provide systems and/or methods to assist individuals manage and/or address associated with physiological arousals through real-time feedback (e.g., real-time biofeedback).

SUMMARY OF THE INVENTION

Disclosed herein is a system for managing physiological arousal with real-time feedback and arousal reduction strategies to treat sleep disorders, for example insomnia. The system uses photoplethysmography (PPG) device equipped with an IR sensor to collect Pulse Wave Amplitude (PWA) data as the only biomarker to reflect physiological arousals. The system further contains a processing unit, for example a mobile application, that connects to a device ring. The processing unit calculates PWA drops which reflect physiological arousal and sympathetic nervous system overactivity. The system in response sends real-time feedback, for example a vibrational signal, to the PPG device to notify the patients to engage in arousal management strategies.

In some forms, the system is a Nocturnal Biofeedback Treatment System for Insomnia (NBTSI), designed to bridge the existing gaps in insomnia treatment. NBTSI integrates a wearable ring device equipped with a photoplethysmography (PPG) sensor and a smartphone application to provide real-time biofeedback during nighttime arousal episodes. By monitoring Pulse Wave Amplitude (PWA), a reliable biomarker of sympathetic nervous system (SNS) activity, NBTSI detects physiological arousals that contribute to insomnia. Upon identifying significant PWA drops, the system alerts the user through vibrational feedback, prompting the engagement of relaxation techniques such as Diaphragmatic Breathing Relaxation (DBR). This seamless integration of wearable technology and mobile health applications offers an autonomous, cost-effective, and user-friendly approach to managing insomnia.

The proposed system addresses the market gaps by providing a real-time, nocturnal biofeedback system that operates autonomously without the need for specialist supervision. The wearable ring device is designed to be lightweight, comfortable, and affordable, making it accessible to a wide range of users. By utilizing a single, validated biomarker (PWA), NBTSI simplifies the biofeedback process, reducing costs and enhancing user convenience. The smartphone application complements the wearable device by processing PWA data, detecting physiological arousal, and delivering real-time feedback to guide subjects through arousal management techniques.

This system empowers subjects to manage their insomnia symptoms directly during sleep disturbances, improving sleep quality and overall health outcomes. Unlike traditional therapies that require scheduled sessions with healthcare professionals, the disclosed system allows individuals to receive immediate feedback and intervention as needed during sleep onset. This autonomy not only enhances the user experience but also encourages consistent use and adherence to relaxation practices, leading to more effective long-term management of insomnia, anxiety, stress, epilepsy, burn out, attention deficit/hyperactivity disorder, or a combination thereof.

DETAILED DESCRIPTION OF THE INVENTION

I. Definitions

Figure 1:
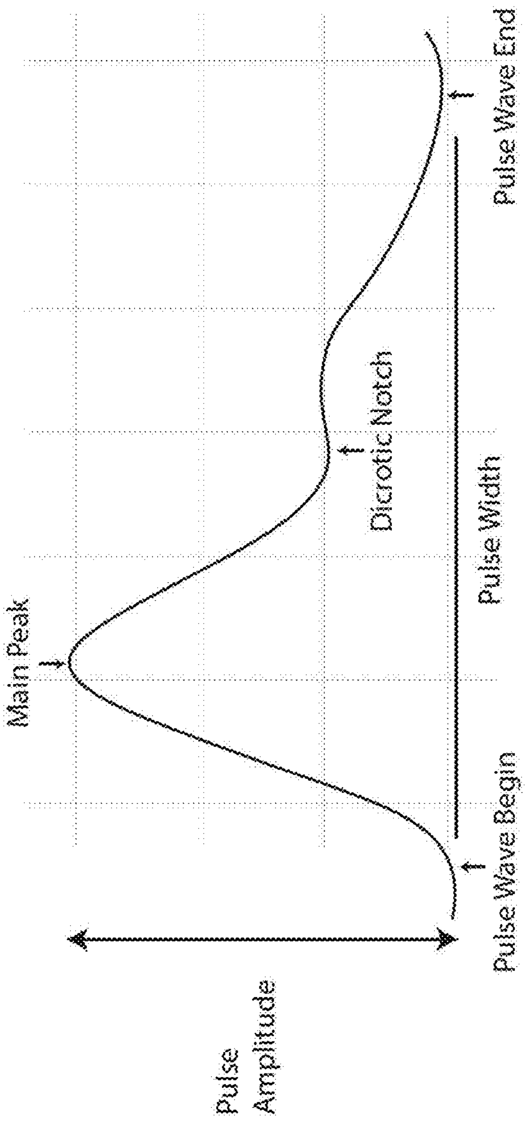
FIG. 1 is a graph showing the Pulse Wave Amplitude (PWA) calculation.

The term "physiological arousal" refers to a state of heightened activity within the autonomic nervous system. Quantitatively, "physiological arousal" can be characterized by a change (e.g., a drop) in Pulse Wave Amplitude of at least 30% from baseline, persisting for at least four heartbeats (about 3 seconds depending on the heartrate).

The term "biofeedback" refers to a process whereby electronic monitoring of a normally automatic bodily function is used to guide/train a subject to acquire voluntary control of that function.

The term "operably linked", refers to the connection of at least two components in a system via technology including, but not limited to, ethernet, Bluetooth, near field communication, WiFi, integrated circuits, or a combination thereof.

The term "pulse wave amplitude", refers to the strength or intensity of a pressure wave that travels through the blood vessels, e.g., arteries. Pulse wave amplitude can provide a measure of how much the artery expands with each heartbeat.

"Continuous monitoring" as relates to a system, tool, or device, refers to a system, tool, or device configured to automatically track, analyze, and/or provide real-time data about a specific environment.

The term "real-time" refers data transmission to a user of a system, tool, or device within 1, 2, 3, 4, 5, 10, 15, 20, or no more than 30 minutes after the system/tool/device receives and/or detects an input signal. The transmitted signal can be a processed signal derived from processing the input signal.

The term "user interface" refers to the means by which a subject and a system or device interact. User interfaces include a human-machine interface (HMI) that typically interfaces systems and devices with physical input hardware, including but not limiting to buttons, switches, microphones, cameras, and pads, and output hardware, including but not limiting to display screens/monitors, speakers, and haptic technology.

"Wearable" as relates to a device, refers to a device that is configured to partially or completely surround a portion of a subject's body; is configured for insertion into an orifice of a subject's body (e.g., ear orifice); and/or is configured for attachment to a portion of a subject's body.

II. Systems

Described are systems containing a wearable device containing a sensor configured to continuously monitor one or more physiological data from a first subject; and a processing unit operably linked to the sensor. The system is configured (a) to process the one or more physiological data into pulse wave amplitude (PWA) data, (b) to calculate changes in the PWA data, and (c) to provide real-time feedback to the first subject or to a second subject. Preferably, calculating changes in the PWA data involves calculating PWA drops indicative of physiological arousal.

In some forms, the described systems have at least photoplethysmography (PPG) device and at least one processing unit for managing physiological arousal with arousal reduction strategies to treat one or more conditions or disorders, such as insomnia, anxiety, stress, epilepsy, burn out, attention deficit/hyperactivity disorder, or a combination thereof. Preferably, the system provides one or more real-time feedback based on real-time data collected by one or more sensors to initiate arousal reduction strategies to manage physiological arousal and treat sleep disorders. Arousal management is generally done through detecting a signal from a subject indicative that the subject is in a state of physiological arousal, followed by sending the subject real-time feedback to initiate arousal management techniques.

In some instances, the system is a Nocturnal Biofeedback Treatment System for Insomnia (NBTSI), wherein the NBTSI has a wearable device and mobile application that provides immediate feedback during episodes of physiological arousal at night to address the limitations of conventional insomnia treatments. This system reduces sleep onset latency by prompting users to engage in arousal management techniques when heightened arousal is detected. Through this interactive approach, the NBTSI enables users to manage insomnia symptoms autonomously, providing an accessible, cost-effective alternative to traditional therapies that often require clinical environments or are limited by high costs and availability.

A. Systems for Physiological Arousal Management

Described is a system for assisting management of physiological arousal in a subject, by detecting pulse amplitude drops followed by outputting at least one real-time feedback, to initiate arousal reduction strategies. Generally, the system for managing physiological arousal includes at least one photoplethysmography (PPG) device and at least one processing unit, operably linked to each other to output real-time feedback to a subject. The subject can be a first subject wearing the device or a second subject not wearing the device. The components of the system can be arranged in any suitable order. In some forms, the PPG device is in the form of a ring configured to monitor and reduce pulse wave amplitude (PWA) in subjects. Additional details about the system's components are provided below.

In some forms, the system uses a ring-like wearable device as the PPG device and a smartphone application as the processing unit. In some forms, the PPG device is configured to continuously monitor Pulse Wave Amplitude (PWA), a biomarker that reflects sympathetic nervous system (SNS) activity. The processing unit receives the PPG data in real time, calculates baseline values, and detects significant PWA drops indicative of physiological arousal. If a PWA drop exceeds a certain threshold from baseline, then the processing unit sends one or more real-time feedback to the subject. In some forms, the real-time feedback is in the form of a LED light alert or vibration alert to the wearable device, encouraging the user to perform relaxation exercises to lower arousal levels and facilitate sleep onset.

1. Photoplethysmography Device

The system includes at least one photoplethysmography (PPG) device operably linked to a processing unit. The at least one PPG device contains at least one infrared sensor and at least one user interface. The PPG device can be in any suitable form that allows it to be used as a wearable device on a subject. Preferably, the PPG device is in the form of a wearable finger-worn ring.

In some forms, the PPG device has an automatic shutdown feature that activates after 10 minutes, 20 minutes, 30 minutes, 40 minutes, 50 minutes, or 60 minutes of stable PWA without significant drops. This conserves battery life and ensures the device remains functional for subsequent nights. If the subject's sleep is disrupted and arousal resumes, the PPG device can be reactivated to restart the monitoring and feedback process. This cycle allows continuous support throughout the night without manual intervention, optimizing the system's effectiveness in sleep management. In some forms, the PPG device is configured to collect PWA data at predetermined intervals to reduce battery consumption.

In some forms, the PPG device is designed to offer subjects a practical and wearable solution for tracking physiological stress indicators for physiological arousals throughout the day. In some forms, the PPG device is constructed to be comfortable and hypoallergenic, enabling extended wear and continuous monitoring during daily activities and sleep. The material choice for the ring prioritizes skin compatibility, minimizing irritation and ensuring durability over long-term use. In some forms, the PPG device exhibits a visually appealing, lightweight design that supports unobtrusive wear, allowing the user to incorporate the device seamlessly into their daily routine. In some forms, the ring body also houses the device's internal components securely, providing structural integrity while remaining visually discreet, which appeals to users seeking a non-invasive, everyday monitoring solution.

i) Infrared Sensor

The sensor is optionally more than one sensor, operably linked with at least one of the other components of the system to collect real-time sensor data from a subject. In some forms, the sensor is an infrared (IR) sensor that captures blood volume changes within the finger, employing a light emitting diode (LED) and photodiode configuration. In some forms, IR sensor is positioned on the inner surface of the ring, in direct contact with the skin. The placement of the IR sensor on the inner ring surface ensures consistent contact with the skin, enhancing the accuracy of data collection and providing a steady stream of information for real-time analysis.

The sensor leverages infrared light to detect and analyze changes in blood flow and volume in the finger, translating these variations into Pulse Wave Amplitude (PWA) data. The LED emits low-intensity infrared light onto the skin, and the photodiode detects the light reflected from blood vessels, producing real-time PPG sensor data. This real-time PPG sensor data is used to calculate the real-time PWA drops and is continuously transmitted to the processing unit. This real-time data collection and analysis allows the system to provide real-time feedback that aligns with the body's immediate physiological state. PWA is a critical metric for evaluating sympathetic nervous system (SNS) activation, which correlates directly with stress levels. By continuously tracking this data, the infrared sensor allows the device to detect shifts in stress levels with high sensitivity.

The real-time sensor inputs and outputs can be communicated to the processing unit wirelessly or via wires, in analog or digital form, intermediated by gating and/or clocking circuits or directly provided.

ii) User Interface

The PPG device includes one or more user interfaces operably linked with the other components of the PPG device for starting and stopping the PPG device, monitoring data collection, and/or delivering real-time feedback to the subject. In some forms, the real-time feedback is provided to the subject via the user interface.

In some forms, the user interface includes a graphical user interface (GUI), menu-driven interface, command line interface, conversational user interface, touch user interface, voice user interface, form-based user interface, natural language user interface, or mobile user interface. In some preferred forms, the user interface includes a GUI.

In some instances, the user interface also provides real-time feedback and monitors real-time data collected and stored, allowing users to view PWA trends and track the impact of relaxation techniques on SNS arousal. Together, these features create a personalized and responsive biofeedback system that not only enhances sleep management at night but also supports daily stress reduction, offering users a comprehensive tool for managing insomnia and improving overall well-being.

In some forms, the user interface features input hardware to Start and Stop the PPG device to provide intuitive access to the monitoring functions and flexibility for activities that may temporarily alter physiological responses, such as exercise or high-intensity movement. This selective control enables the subject to maintain more accurate monitoring results that reflect periods of typical stress and relaxation, supporting the device's goal of providing reliable, actionable data. In some forms, the user interface contains input hardware for setting relaxation goals and tracking progress.

In some forms, the user interface includes LED Battery Level Indicators that communicate power status through a simple color-coded display. This indicator provides three levels of battery information: green for full charge, yellow for medium charge, and red for low battery. By visually indicating the battery level, the PPG device helps the user manage power consumption and ensures they can recharge the device before it runs out of power. This feature maintains continuous stress monitoring, particularly for users who rely on real-time feedback throughout their day.

a) Real-Time Feedback

The system includes the provision that at least one real-time feedback based on the real-time data provided by the PPG device and processing unit is delivered to the subject from the user interface operably linked with the other components of the system once the subject exhibits physiological arousal. In some forms, the user interface includes auditory feedback systems, haptic feedback systems, and/or visual feedback systems. The real-time feedback delivered by the user interface can be an alert, message, notification, or a combination thereof, that the subject is exhibiting or has stopped exhibiting physiological arousal, and/or a directive for the subject to engage in arousal reduction strategies. In some forms, the real-time feedback is in the form of executable program or application stored in the PPG device that engages with the subject.

The real-time feedback mechanism is based on SNS activity, as measured by PWA changes. SNS overactivity is known to contribute to insomnia by triggering physiological arousal that disrupts sleep. By identifying PWA drops, which correspond to vasoconstriction and increased SNS activation, the device provides a practical marker for detecting heightened arousal states. The PPG device features a user interface to provide positive reinforcement and/or to act as a signal to the subject to refocus on arousal reduction strategies. In some forms, the arousal reduction strategies are breathing exercises, visualization exercises, or muscle relaxation exercises. Preferably, the arousal reduction strategies are breathing exercises such as Diaphragmatic Breathing Relaxation (DBR).

In some forms, the PPG device encourages the use of DBR as the primary technique to mitigate arousal. DBR is a proven method for reducing SNS activity by promoting deep, rhythmic breathing, which supports sleep initiation. In some forms, the real-time feedback includes step-by-step instructions for conducting arousal reduction strategies, helping users engage in this technique as soon as an alert is received. The interactive nature of this approach empowers users to effectively manage their insomnia symptoms through self-guided intervention.

In some forms, the user interface includes an auditory feedback system. In some instances, the auditory feedback systems include speakers to provide auditory output, which may include feedback sounds, alerts, or other forms of audio communication relevant to the device's purpose. In some instances, the auditory feedback system delivers an auditory signal, such as a satisfaction sound, when the user achieves a target reduction in PWA of less than 5%, 10%, 15%, 20%, 25%, 30%, 35%, or 40%. In this instance, the feature provides immediate reinforcement to encourage relaxation. By employing this mechanism, the device effectively aids in supporting sleep by facilitating physiological states conducive to relaxation.

In some forms, the user interface includes a haptic feedback system. In some forms, the haptic feedback system contains vibration motors that alert the subject to significant increases in physiological arousal. Specifically, when a drop of 5%, 10%, 15%, 20%, 25%, 30%, 35%, 40% or more in PWA is detected, indicating heightened SNS activity and, therefore, physiological arousal, the vibration motor activates, delivering a gentle but noticeable vibration. In this instance, the haptic alert serves as an immediate, non-intrusive prompt for the user to engage in relaxation techniques or other stress-management strategies. In this instance, the vibration motors are calibrated to avoid disruption while still providing sufficient feedback to raise awareness, allowing users to respond promptly to stress spikes without interrupting their current activities.

In some instances, the intensity and duration of the vibration motors can be adjusted through the user interface, allowing users to tailor the biofeedback experience to their preferences. In some instances, the sensitivity of the PPG device to PWA drops can be modified through the user interface. This feature ensures that during periods of intense physical activity, users can reduce false positives during exercise or other exertive tasks.

In some forms, the user interface includes a visual feedback system. In some forms, the visual feedback system includes LED light indicators to function as Arousal Level Indicators on the outer surface of the ring for a visual representation of physiological arousal. In this instance, the LED light indicator uses a three-color system—green, yellow, and red—to communicate the user's current stress level based on SNS activation. A green light represents baseline or low SNS activation, indicating a calm state with minimal stress. A yellow light signals moderate SNS activation, suggesting a mild increase in stress that may require attention. The red light indicates high SNS activation, alerting the user to significant stress levels that may need immediate intervention. This LED indicator allows for quick visual assessment, empowering users to monitor their stress throughout the day without the need to check a digital screen or external device.

2. Processing Unit

The system or device includes at least one processing unit, operably linked with at least one of the other components of the system for processing and storing the real-time sensor data collected by the at least one sensor and outputting a real-time feedback to initiate arousal reduction strategies.

The one or more processing units for processing the signals can be, for example, one or more computing processors. In some forms, the computer processor is a microprocessor, a single-core processor or a multiple-core processor, a single-core processor configured with virtual processing technologies, logical processors to simultaneously execute and control multiple processes. In some forms, the one or more processing units implement technologies such as virtual-machine technologies to execute, control, run, manipulate, and/or store multiple processes, applications, and/or programs. In some forms, the one or more processing units include a multiple-core processor configured to provide parallel processing functionalities for execution of multiple processes simultaneously. In some forms, the one or more processing units are configured, for example, to execute one or more instructions stored in memory to perform operations. In some forms, the one or more processing units are in the form of a laptop, computer, server, tablet, or a smartphone. Preferably, the processing unit is in the form of an application on a smartphone.

In some forms, the processing unit is a smartphone application that logs data on PWA fluctuations, real-time feedback, and user engagement with relaxation techniques. This data can be reviewed by users to track their progress and identify patterns in arousal and sleep latency. In some forms, the smartphone application features a user feedback loop system that provides insights that help subjects understand their arousal triggers and refine their relaxation response over time, fostering improved sleep habits and a greater sense of control over insomnia symptoms. This user feedback loop system allows the subject to refine relaxation prompt timing based on the subject's response history. In some forms, the smartphone application resamples the PWA data to improve signal accuracy before PWA drop calculation. In some forms, the smartphone application includes a machine learning algorithm to detect and classify PWA drop patterns over time. In some forms, the smartphone application provides visual and textual guidance on Diaphragmatic Breathing Relaxation (DBR).

In some forms, the smartphone application filters out noise and artifacts from PPG data prior to calculating PWA. In some forms, the smartphone application includes visual and textual guidance on Diaphragmatic Breathing Relaxation (DBR). In some forms, the smartphone applications allow subjects to set personalized reminders or alarms for engaging in relaxation techniques. In some forms, the smartphone application allows subjects to set relaxation goals and track progress. In some forms, the smartphone application provides subjects with daily, weekly, and/or monthly summaries of their sleep data and biofeedback session outcomes. In some forms, the processing unit and the PPG device are unified in one device.

B. Exemplary Systems and Devices for Physiological Arousal Management

Figure 7:
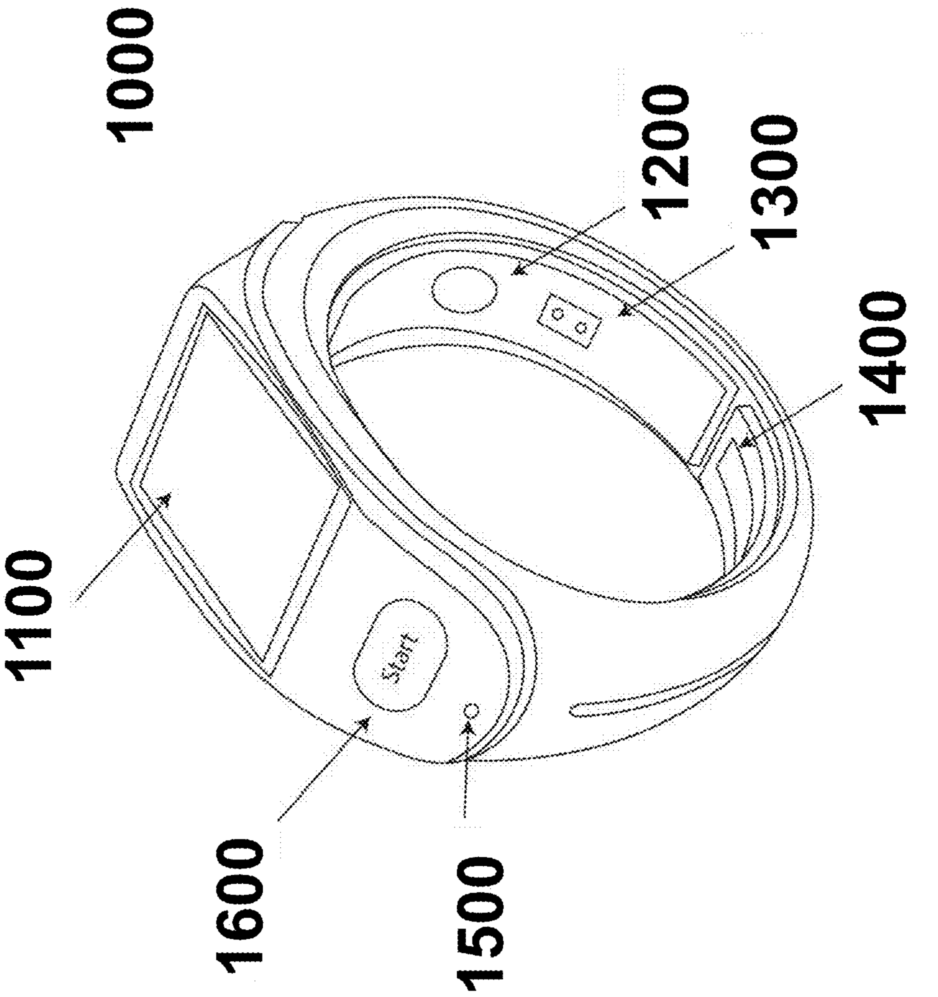
FIG. 7 is a schematic of an exemplary sensor for detecting physiological arousal and sympathetic nervous system activity.

FIG. 7 is a schematic depicting an exemplary device physiological arousal management. As shown in FIG. 7, exemplary device 1000 features external and functional components designed to support operational and interactive capabilities. The user interface features a "Start/Stop" button 1600, which serves as the primary control for initiating and terminating the device's functionality. This feature ensures simple and intuitive operation. Accompanying this is a speaker 1500, positioned to provide auditory output, which may include feedback sounds, alerts, or other forms of audio communication relevant to the device's purpose. The GUI, 1100, prominently displayed, presents visual feedback, such as progress metrics, system status, or user instructions, ensuring clarity and ease of use.

The device further incorporates an infrared sensor, 1200, strategically placed to collect physiological data, such as monitoring pulse wave amplitude (PWA) or other biometric parameters. A vibrations unit, 1400, is also included, which could be utilized to deliver tactile feedback, enhancing the user experience through non-intrusive alerts or reinforcement cues. Finally, a charging port, 1300, allows the device to operate with a rechargeable power source, emphasizing portability and convenience. Collectively, these components support both the device's core functionality and subject's engagement.

III. Methods of Using

The system disclosed herein can be used for assisting subjects to manage one or more conditions or disorders. Preferably, the one or more conditions or disorders are associated with the activity of a subject's sympathetic nervous system. In some forms, the one or more conditions or disorders include insomnia, anxiety, stress, epilepsy, burn out, attention deficit/hyperactivity disorder, or a combination thereof. Preferably, the disorder is insomnia. The system allows patients to interactively mentor and control their physiological and cognitive arousal that are known to activate the sympathetic nervous system (SNS) (Jerath et al., 2019; Levenson et al., 2015). Thus, the system uses the SNS activity as an indicator for the physiological and cognitive arousals that patients need to control to initiate sleep. In some instances, the system features a vibration feedback component in ring with a high sensitivity to SNS activity. For example, the system notifies the subject to control their thoughts and tensive body which prevents them from sleeping.

The disclosed system measures SNS activation using the PWA drops. PWA is defined as difference between the highest point (peak) and lowest point (nadir) value of the pulse wave at each cardiac cycle. FIG. 1 illustrates the calculation of Pulse Wave Amplitude (PWA), highlighting the difference between the peak (highest point) and lowest point of each pulse wave cycle. This figure serves as a foundational visualization of how PWA reflects SNS activity, making it a suitable biomarker for detecting arousal states that could interrupt sleep. The PWA measurement forms the basis for the system's biofeedback intervention, enabling precise detection of arousal levels that may delay sleep onset. FIG. 1 moreover showcases various elements of a pulse waveform measurement taken from an exemplary PPG device, such as a ring that monitors cardiovascular health. The waveform details include the "Main Peak," indicating the highest point in pulse pressure, followed by the "Dicrotic Notch," which represents a brief decrease in pressure within the artery marking the end of systolic expansion. Various phases including the "Pulse Wave Begin," "Pulse Width," and "Pulse Wave End" are clearly marked, explaining the entire pulse cycle duration and its amplitude. Key intervals and pulses are plotted against time (x-axis) and voltage (V) (y-axis), emphasizing the dynamics and health of the cardiovascular pulse waveforms in the individual wearing the device.

Figure 2:
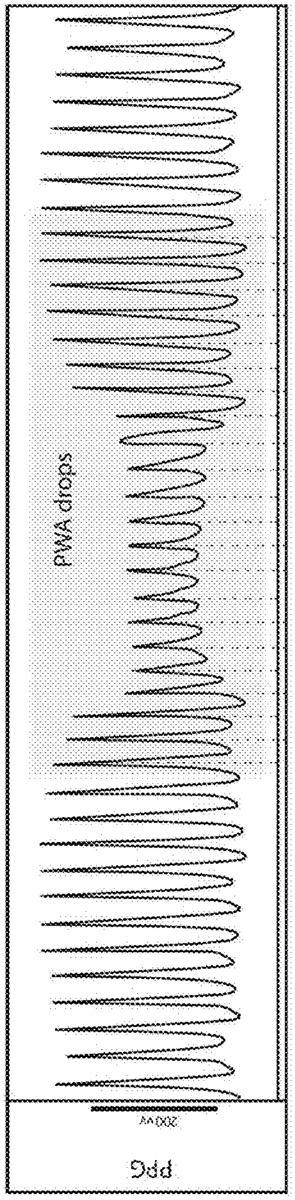
FIG. 2 is a graph showing the PWA in the yellow highlighted part of the photoplethysmogram (PPG) data.

The PWA drops is used as a marker of finger vasoconstriction (Catcheside et al., 2002), reflected by decreases in the signal amplitude (PWA drops) as a surrogate of autonomic and cortical arousal (Catcheside et al., 2002; Haba-Rubio et al., 2005) (FIG. 2). PWA drops has been validated as a measurement of SNS activation (Alomri et al., 2021; Hamunen et al., 2012). FIG. 2 demonstrates a typical PPG graph, with specific emphasis on the highlighted yellow sections that indicate drops in PWA. These drops correspond to periods of SNS activation and arousal. This figure illustrates how the system identifies and interprets PWA drops in real-time to trigger biofeedback interventions, thereby helping users manage sleep-related arousal in a timely manner.

Figure 3:
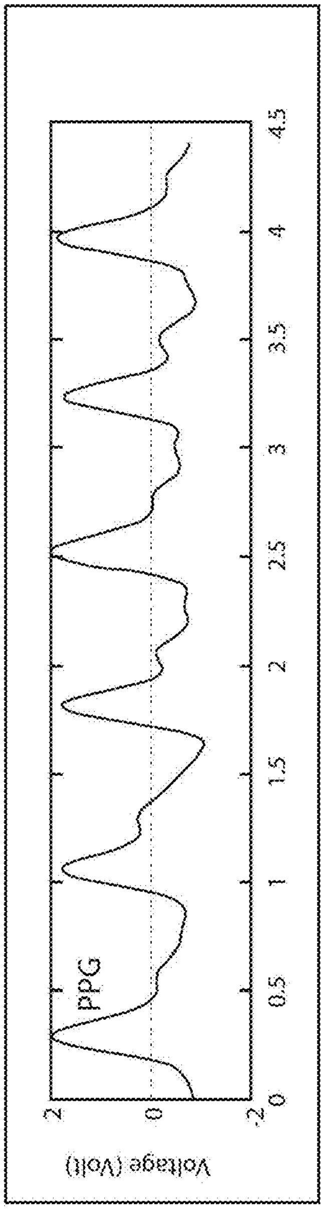
FIG. 3 is a graph showing the PWA data.

PWA is based on the PPG data (FIG. 3) that is obtained from the conventional pulse oximetry (British et al., 1954). FIG. 3 shows the PPG data flow from the PPG device to the processing unit. In preferred forms, the data transmission relies on Bluetooth, enabling the real-time transfer of physiological measurements. This design allows the processing unit to promptly analyze PPG data, calculate baseline and drop thresholds, and deliver feedback mechanisms when arousal is detected. In some instances, the PPG device collects the PPG data and transmit it to the patient's smartphone using a Bluetooth module that allows these devices to communicate, send and receive data from each other in real time. The PPG data is obtained by utilizing a light-emitting diode (LED) to generate low-intensity infrared light on the skin, the non-absorbed light will be reflected and detected by a photodiode.

Figure 4:
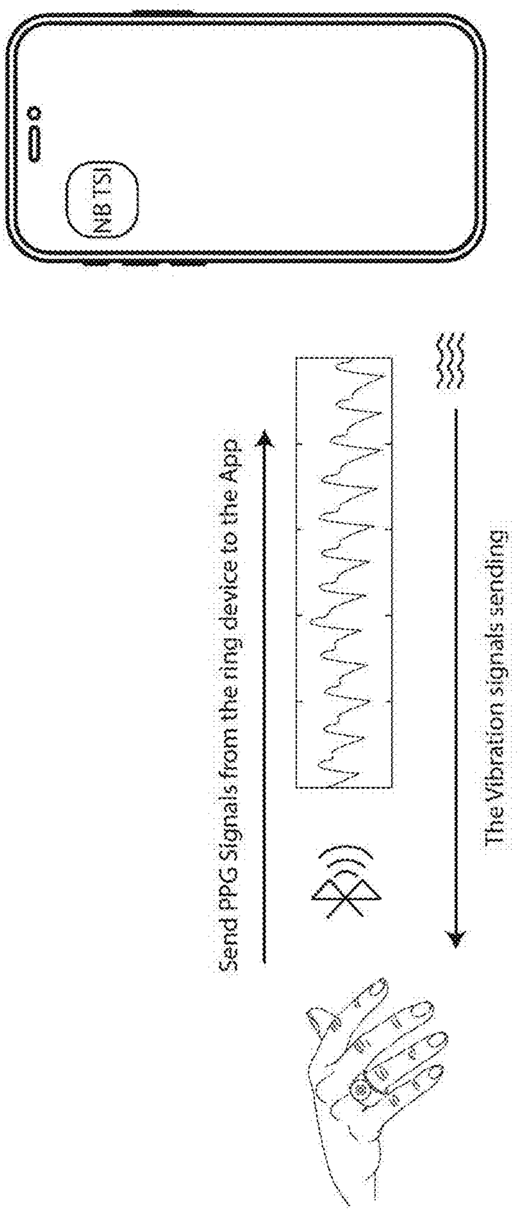
FIG. 4 is a work-flow diagram showing the communication between the ring device and the smartphone application.

FIG. 4 discloses the sequence of steps starting from the moment an individual is preparing for sleep wearing a specialized ring device up to the evaluation if the person should commence sleep based on the measurement of physiological wave amplitudes. The first step involves the patient wearing the ring device five minutes prior to bed, allowing it to establish a baseline reading of pulse wave amplitude (PWA). If there's a significant reduction (≥30%) in the PWA from this baseline during the pre-sleep phase, the ring briefly vibrates to alert the user. This alert is an indication for the individual to manage their physical and mental state to conquer sleep initiation difficulties, by engaging in suggested relaxation tactics like diaphragmatic breathing and not engaging in mentally stimulating activities. After re-evaluating if the PWA drop is below 30%, if affirmative, the individual can proceed to sleep, with the device turning off after 30 minutes if there are no further disruptions in PWA. For example, Stromberg et al. and Aslan et al. revealed that DBRT is an efficacious intervention that enhances sleep and decreases anxiety & depression as deep breathing inhibits sympathetic activation by the cardiopulmonary synchronization (Liu et al., 2021). Finally, after five minutes if the PWA drops are still greater or equal 30% from the baseline the ring device will vibrate again. In the case of no PWA drops for more than 30 minutes, the device will be automatically turned off. When the subject's sleep has been disrupted, they need to turn on the device to start the treatment again.

Figure 5:
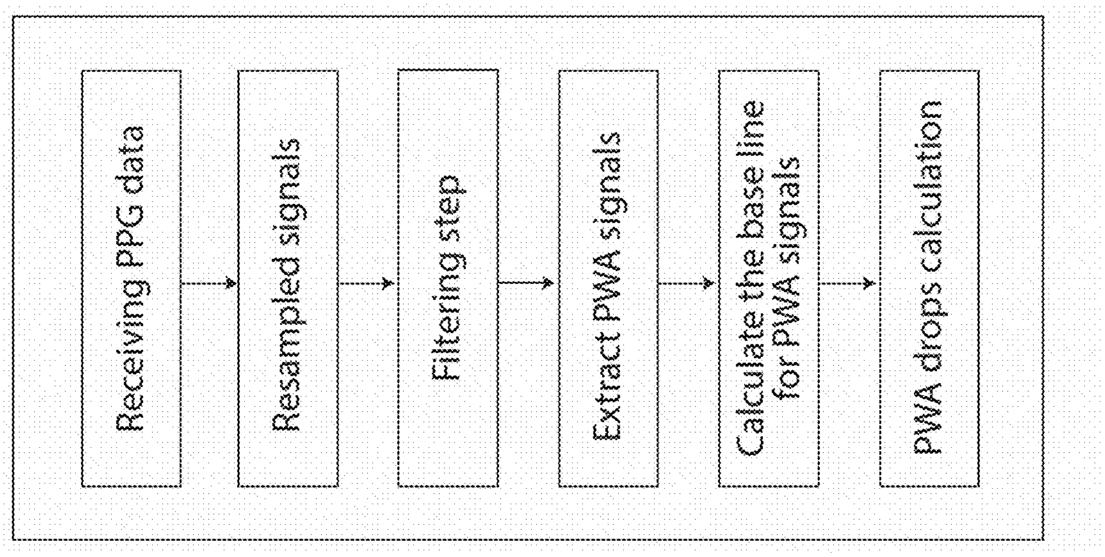
FIG. 5 is a work-flow diagram indicating the photoplethysmogram (PPG) data signal processing in the mobile application.

The processing unit receives and analyzes the PPG data to extract the PWA signal and detect the PWA drops. FIG. 5 covers the extraction and processing of PWA signals to determine their suitability for notifying the user of potential sleep disruptions. Initially, the data is drawn from the PPG device that captures vibration and peripheral pulse signals. Once the PWA signals are gathered, they undergo a resampling and filtering process to prepare for accurate analysis. Subsequently, an algorithm calculates the baseline PWA and detects any significant drop in PWA relative to this base level. If the calculated values meet specific decline thresholds (e.g., ≥30%), it sets off the device's notification mechanism which ultimately guides the user to adjust their mental and physical state appropriately in preparation for sleep. As illustrated in FIG. 5, PPG data will be resampled signals before passing to the filter step. In the filter step, the noise and other artifacts will be removed from the PPG signals. Then, the PWA signals will be extracted. The PWA signal is the difference between the highest point (peak) and lowest point (nadir) value at each cardiac cycle. In the phase of baseline calculation, the processing unit will calculate the baseline for PWA signals after the 4th heartbeat. Finally, PWA drops calculation is applied based on the previous studies. For instance, since spontaneous variations of PWA in the magnitude of 10-30% may reflect normal oscillations of the autonomic nervous system in healthy subjects, PWA drops with an amplitude >30% and a duration >4 heartbeats were identified (Alomri et al., 2021; Bosi et al., 2018; Hirotsu et al., 2020). Valid PWA-drops are required to be longer than 3 seconds (Bosi et al., 2018; Hirotsu et al., 2020). If the processing unit detects the PWA drops, the notification vibration will send to the PPG device.

Figure 6:
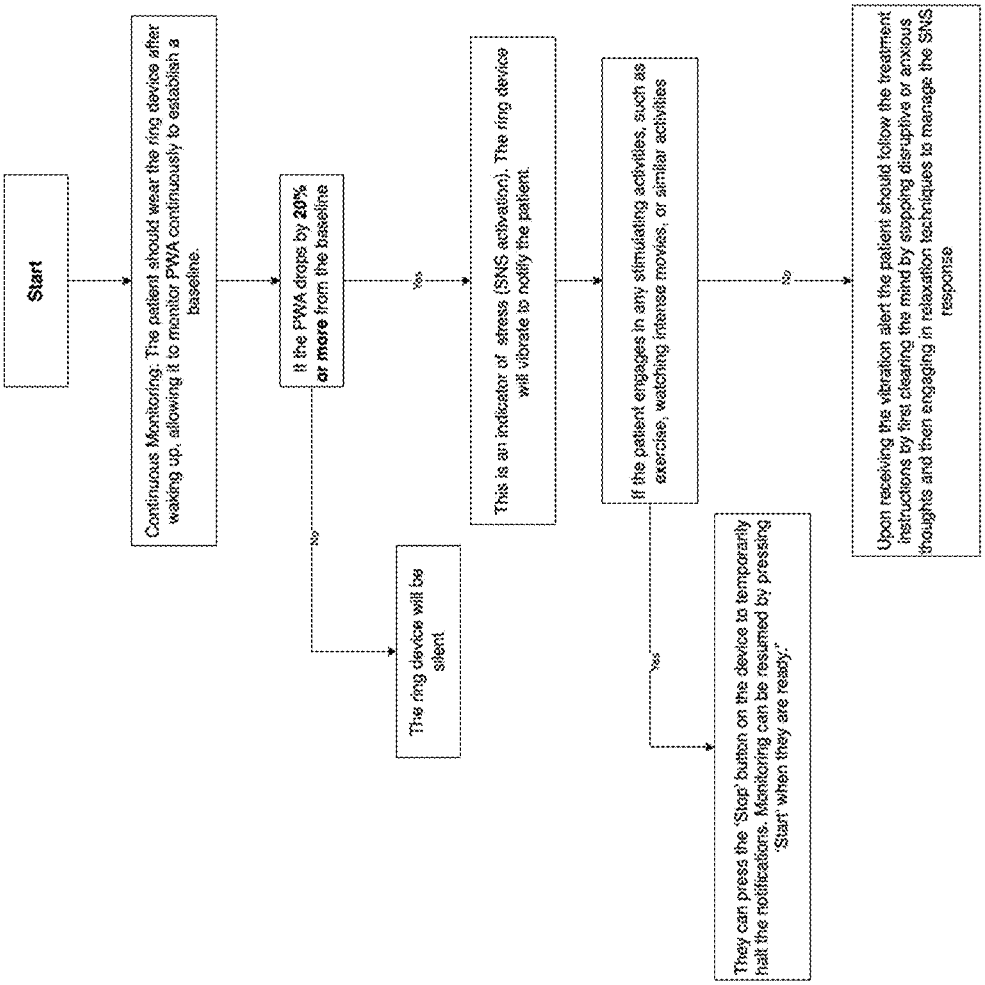
FIG. 6 is a work-flow diagram showing the system process.

FIG. 6 illustrates the process of the system disclosed herein. This figure provides a structured overview of how the system operates to manage insomnia through a feedback mechanism designed for nighttime use. The system is structured around monitoring and responding to physiological data, including heart rate, breathing patterns, or other indicators that reflect sleep states or stress levels. The biofeedback approach ensures that users are provided real-time data about their physical states, allowing them to recognize when they're experiencing sleep disturbances and, with training, adjust their mental or physical responses to encourage better sleep.

The process of the system disclosed herein includes several stages, from initial data capture to processing and then to feedback delivery. The system may operate autonomously or require user input, possibly showing visual or auditory cues to guide users toward behaviors that promote relaxation or sleep. In some preferred instances, the system focuses on nocturnal biofeedback. By focusing on nocturnal biofeedback, the system provides targeted support during the hours when sleep disorders, such as insomnia, typically disrupts users, which can reinforce positive sleep behaviors over time. This approach may also help subjects develop long-term skills for managing insomnia, as they learn to interpret and respond to the feedback signals even outside of the system sessions.

It should be noted that while the design of the system described herein emphasizes ease of use and seamless integration into the user's nightly routine, the system can also be used by a subject during the day. The wearable device (e.g., wearable ring) is intuitive and requires minimal setup, while the mobile application offers a straightforward interface for monitoring and managing sleep data. Other data that can be monitored and/or managed by the system include anxiety, stress, epilepsy, burn out, attention deficit/hyperactivity disorder, or a combination thereof. This simplicity ensures that users of all technical proficiencies can effectively utilize the system without encountering barriers related to complexity or user-friendliness.

By continuously monitoring PWA in real-time, the system provides immediate detection of physiological arousal events that may give rise to insomnia, anxiety, stress, epilepsy, burn out, attention deficit/hyperactivity disorder, or a combination thereof. This real-time capability ensures that interventions are timely and relevant, increasing the likelihood of successful management of one or more of these conditions or disorder. In some form, this includes increasing the likelihood of successful sleep initiation and maintenance. The continuous monitoring also allows for the collection of valuable data related to insomnia, anxiety, stress, epilepsy, burn out, attention deficit/hyperactivity disorder, or a combination thereof, which can be used to personalize and optimize treatment protocols over time.

The system is designed to be a cost-effective solution compared to existing biofeedback and virtual reality-based systems. By utilizing a single PPG sensor and leveraging existing smartphone technology, the overall production and operational costs are significantly reduced. This affordability makes the system accessible to a larger population, democratizing access to effective insomnia treatment and reducing the financial barriers associated with traditional therapies.

The compact and portable nature of the wearable device (e.g., wearable ring ensures) that users can easily incorporate the system into their daily lives without inconvenience. Unlike bulky devices, the wearable device (e.g., wearable ring) is discreet and can be worn comfortably throughout the night and/or daytime, allowing users to maintain their usual night time and/or daytime environment and habits without disruption.

The system incorporates evidence-based relaxation techniques, such as diaphragmatic breathing relaxation (DBR), which have been scientifically validated to reduce SNS activity and promote relaxation. By integrating these techniques into the biofeedback system, the system ensures that users are guided through effective practices that directly address the physiological and cognitive factors contributing to insomnia, anxiety, stress, epilepsy, burn out, attention deficit/hyperactivity disorder, or a combination thereof.

The mobile application associated not only provides real-time feedback but also logs and analyzes relevant data over time, including sleep data. In the case of insomnia, this data-driven approach allows users to track their progress, identify patterns, and make informed decisions about their sleep habits and relaxation practices. The ability to review historical data enhances the user's understanding of their sleep dynamics and supports continuous improvement in sleep management.

The system is designed to be scalable and adaptable to various user needs and environments. The system can accommodate different user patterns and preferences, allowing for customization of alert thresholds and relaxation prompts. This flexibility ensures that the system can be effectively utilized by a diverse user base, catering to individual differences in behavior and physiological responses associated with insomnia, anxiety, stress, epilepsy, burn out, attention deficit/hyperactivity disorder, or a combination thereof.

By providing a non-invasive, self-administered treatment option, the system promotes sustainable health outcomes for individuals with insomnia, anxiety, stress, epilepsy, burn out, attention deficit/hyperactivity disorder, or a combination thereof. The continuous use of biofeedback and relaxation techniques can lead to lasting improvements in quality of life for subjects with one or more of these conditions or disorders, reducing reliance on short-term pharmacological treatments, and/or minimizing the risk of associated side effects. This sustainable approach aligns with modern healthcare goals of promoting long-term well-being and preventative health measures.

Use of the disclosed system represents a significant advancement in the management of insomnia, anxiety, stress, epilepsy, burn out, attention deficit/hyperactivity disorder, or a combination thereof, by addressing key limitations of existing therapies. Through its innovative integration of wearable technology and mobile health applications, the system offers a real-time, cost-effective, and user-friendly solution that empowers individuals to manage their behaviors autonomously.

The disclosed systems and methods of using can be further understood through the following enumerated paragraphs or embodiments.

1. A system containing:

(i) a wearable device containing a sensor configured to continuously monitor one or more physiological data from a first subject; and (ii) a processing unit operably linked to the sensor;

wherein the system is configured (a) to process the one or more physiological data into pulse wave amplitude (PWA) data, (b) to calculate changes in the PWA data, and (c) to provide real-time feedback to the first subject or to a second subject.

2. The system of paragraph 1, wherein calculating changes in the PWA data comprises calculating PWA drops indicative of physiological arousal.

3. The system of paragraph 1 or 2, wherein the sensor contains a photoplethysmography (PPG) sensor.

4. The system of any of the preceding paragraphs, wherein the sensor contains a light-emitting diode and a photodiode.

5. The system of any of the preceding paragraphs, wherein the system contains executable instructions executed by the processor to analyze the PWA data stored in the system to establish baseline measurements for the subject.

6. The system of paragraph 5, wherein the executable instructions are capable of filtering out noise artifacts from the one or more physiological data prior to generating the PWA data.

7. The system of any of the preceding paragraphs, wherein the executable instructions are capable of resampling the one or more physiological data to improve signal accuracy prior to calculating changes in the PWA data.

8. The system of any of the preceding paragraphs, wherein the wearable device has a ring shape.

9. The system of any of the preceding paragraphs, wherein the wearable device is configured to automatically deactivate if no PWA changes are detected within a predetermined period, optionally within 10 minutes, 20 minutes, 30 minutes, 40 minutes, 50 minutes, or 60 minutes.

10. The system of any of the preceding paragraphs, wherein the wearable device contains speakers, vibration motors, and LED light indicators, optionally wherein the wearable device comprises input hardware to modify the duration and intensity of the vibration motors.

11. The system of any of the preceding paragraphs, wherein the real-time feedback comprises tactile feedback (e.g., vibrational alerts), audio feedback, visual feedback, thermal feedback, or a combination thereof.

12. The system of any of the preceding paragraphs, configured to operate in offline mode, with the one or more physiological data and real-time feedback provided without requiring internet connectivity.

13. The system of any of the preceding paragraphs, wherein the one or more physiological data include blood flow, blood flow volume, blood flow volume change, blood pulse volume, breathing rate, heart rate, or a combination thereof.

14. The system of any of the preceding paragraphs, configured to provide the real-time feedback to the first subject or second subject once changes in the PWA data indicate a PWA drop of 5%, 10%, 15%, 20%, 25%, 30%, 35%, 40% or more from an established PWA baseline.

15. The system of any of the preceding paragraphs, containing a machine learning algorithm to detect and classify PWA drop patterns over time.

16. A method for managing and/or treating one or more conditions or disorders in a first subject in need thereof, the method involving attaching the system of any of the preceding paragraphs to the first subject.

17. The method of paragraph 16, wherein the one or more conditions or disorders are relatable to activities associated with the first subject's sympathetic nervous system.

18. The method of any of the preceding paragraphs, wherein the one or more conditions or disorders include insomnia, anxiety, stress, epilepsy, burn out, attention deficit/hyperactivity disorder, or a combination thereof.

19. The method of any of the preceding paragraphs, further involving:

providing guided relaxation prompts including diaphragmatic breathing exercises, upon detection of significant sympathetic nervous system activity as indicated by a drop in PWA of 5%, 10%, 15%, 20%, 25%, 30%, 35%, 40% or more from an established PWA baseline.

20. The method of any of the preceding paragraphs, further involving:

logging and/or analyzing user data over time, including PWA fluctuations, frequency of alerts, and user engagement with relaxation prompts, and optionally generating reports to allow users to track and understand patterns related to stress and sleep disturbances.

21. A Nocturnal Biofeedback Treatment System for Insomnia (NBTSI) containing:

a wearable ring device configured to measure Pulse Wave Amplitude (PWA) data to detect physiological arousal associated with the sympathetic nervous system, and a mobile application configured to analyze the PWA data, to calculate PWA drops indicative of physiological arousal, and to communicate with the wearable ring device to alert a user through one or more vibrational alerts to engage in relaxation techniques for managing insomnia.

22. The system of paragraph 21, wherein the wearable ring device is equipped with a photoplethysmography (PPG) sensor to measure PWA.

23. The system of paragraph 21 or 22, configured to trigger an alert when the PWA drop is greater than 30% from an established baseline.

24. The system of any one of paragraphs 21 to 23, wherein the mobile application is configured to store and to analyze PWA data to establish individual baseline measurements for each user.

25. The system of any one of paragraphs 21 to 24, wherein the wearable ring device communicates with the mobile application via a Bluetooth module.

26. The system of any one of paragraphs 21 to 25, wherein the mobile application is configured to filter out noise and artifacts from PPG data prior to calculating PWA.

27. The system of any one of paragraphs 21 to 26, wherein duration and intensity of the one or more vibrational alerts are customizable based on user preference.

28. The system of any one of paragraphs 21 to 27, wherein the wearable ring device is designed to automatically deactivate if no PWA drops are detected for a predetermined period, such as 30 minutes.

29. The system of any one of paragraphs 21 to 28, wherein the mobile application provides real-time prompts to the user based on PWA data analysis, the prompts instructing the user to engage in relaxation techniques such as Diaphragmatic Breathing Relaxation (DBR) when physiological arousal is detected.

30. The system of any one of paragraphs 21 to 29, wherein the mobile application includes visual and textual guidance on Diaphragmatic Breathing Relaxation (DBR).

31. The system of any one of paragraphs 21 to 30, wherein the mobile application is configured to track and to log the frequency and duration of PWA drops and user responses.

32. The system of any one of paragraphs 21 to 31, wherein the mobile application is configured to provide a user feedback loop to refine relaxation prompt timing based on the user's response history.

33. The system of any one of paragraphs 21 to 32, wherein the mobile application is configured to allow users to set personalized reminders or alarms for engaging in relaxation techniques.

34. The system of any one of paragraphs 21 to 33, wherein the mobile application includes a user interface for setting relaxation goals and tracking progress 35. The system of any one of paragraphs 21 to 34, wherein the application incorporates audio or visual prompts in addition to the one or more vibrational alerts to guide relaxation exercises.

36. The system of any one of paragraphs 21 to 35, wherein the application provides users with daily, weekly, or monthly summaries of their sleep data and biofeedback session outcomes.

37. The system of any one of paragraphs 21 to 36, wherein the wearable ring device is configured to measure and to transmit photoplethysmographic (PPG) data in real-time to the mobile application for PWA drop analysis and to provide real-time biofeedback to mitigate cognitive and physiological arousal through interactive biofeedback.

38. The system of any one of paragraphs 21 to 37, wherein the wearable ring device includes an LED and photodiode to capture PPG data by emitting and detecting infrared light.

39. The system of any one of paragraphs 21 to 38, wherein the wearable ring device is configured to collect PPG data at predetermined intervals to reduce battery consumption.

40. The system of any one of paragraphs 21 to 39, wherein the wearable ring device is configured to store PPG data locally if a connection with the mobile application is temporarily lost.

41. The system of any one of paragraphs 21 to 40, wherein the mobile application is configured to resample the PPG data to improve signal accuracy before PWA drop calculation.

42. The system of any one of paragraphs 21 to 41, wherein the mobile application includes a machine learning algorithm to detect and classify PWA drop patterns over time.

43. The system of any one of paragraphs 21 to 42, wherein the mobile application is configured to display real-time biofeedback data, allowing the user to view immediate effects of their relaxation efforts on physiological arousal.

44. The system of any one of paragraphs 21 to 43, wherein the wearable ring device and the mobile application are configured to operate in offline mode, with PPG data and feedback provided locally, without requiring internet connectivity.

45. A Nocturnal Biofeedback Treatment System, containing:

a wearable ring device configured for continuous wear throughout the day to monitor stress and/or reduce sympathetic nervous system (SNS) activation, thereby aiding in sleep preparation;

a photoplethysmography (PPG) sensor within the wearable ring device to measure Pulse Wave Amplitude (PWA), allowing for continuous detection of SNS activity related to stress and physiological arousal; and a mobile application operably linked to the ring device to process PWA data, calculate baseline measurements, and identify significant drops in PWA that indicate stress or arousal states, wherein said mobile application is configured to trigger vibrational alerts through the ring device upon detecting PWA drops exceeding a threshold level.

46. The system of paragraph 45, wherein the PWA measurement technology is selected over Heart Rate Variability (HRV) due to enhanced accuracy of the PWA in detecting stress under conditions involving body movement or positional changes, thereby providing a more consistent method for real-time stress detection and sleep support.

47. The system of paragraph 45 or 46, further containing a user-activated button on the wearable ring device, configured to allow the user to adjust biofeedback sensitivity settings during physical activities, such as exercise, to prevent misinterpretation of exertion-related arousal as stress.

48. The system of any one of paragraphs 45 to 47, wherein the mobile application is further configured to provide guided relaxation prompts, including Diaphragmatic Breathing exercises, upon detection of significant SNS activity as indicated by a drop in PWA, thus promoting relaxation and facilitating sleep onset.

49. The system of any one of paragraphs 45 to 48, wherein the mobile application is configured to log and to analyze user data over time, including PWA fluctuations, frequency of alerts, and user engagement with relaxation prompts, thereby generating reports to allow users to track and understand patterns related to stress and sleep disturbances.

50. The system of any one of paragraphs 45 to 49, further containing a technical drawing of the wearable ring device, depicting its material composition, structural design, and key internal components that facilitate its comfort and durability for continuous daily wear.

51. The system of any one of paragraphs 45 to 50, wherein the vibrational alerts have intensity and duration that are customizable by the user through the mobile application to tailor the feedback experience to individual preferences.

52. The system of any one of paragraphs 45 to 51, wherein the wearable ring device includes an automatic power-down feature that activates when no significant PWA drops are detected for a specified period, such as 30 minutes, to conserve battery life and ensure reliable nighttime use.

53. The system of any one of paragraphs 45 to 52, wherein the mobile application is configured to provide real-time graphical feedback to the user, displaying PWA trends and arousal events, thereby enabling the user to observe the immediate effects of relaxation techniques on physiological arousal.

Those skilled in the art will recognize, or be able to ascertain using no more than routine experimentation, many equivalents to the specific embodiments of the invention described herein. Such equivalents are intended to be encompassed by the following claims.

We claim:

1. A system comprising:

(i) a wearable ring device comprising a photoplethysmography (PPG) sensor, a vibration motor, and at least one user-actuated button, wherein the sensor is configured to continuously monitor one or more physiological data from a first subject; and (ii) a mobile application in communication with the wearable ring device;

wherein:

(a) the wearable ring device is configured to, in response to actuation of the user-actuated button, initiate establishment of a baseline PWA value from PPG signal data acquired following said actuation;

(b) the system is configured to monitor subsequent PWA values against said baseline and to cause the vibration motor to deliver a haptic alert upon detecting a PWA drop exceeding a predetermined threshold from said baseline; and (c) the mobile application is configured to process PPG data received from the wearable ring device and to coordinate alert and/or relaxation-prompt functions of the system.

2. The system of claim 1, wherein the PWA drop comprises calculating PWA drops indicative of physiological arousal.

3. The system of claim 1, wherein the PPG sensor comprises a light-emitting diode and a photodiode.

4. The system of claim 1, wherein the system comprises executable instructions executed by the processor to analyze the PWA data stored in the system to establish baseline measurements for the subject.

5. The system of claim 4, wherein the executable instructions are capable of:

(i) filtering out noise artifacts from the one or more physiological data prior to generating the PWA data; and/or (ii) resampling the one or more physiological data to improve signal accuracy prior to calculating changes in the PWA data.

6. The system of claim 1, wherein the wearable ring device is configured to automatically deactivate if no PWA changes are detected within a predetermined period, optionally within 10 minutes, 20 minutes, 30 minutes, 40 minutes, 50 minutes, or 60 minutes, wherein the predetermined period is measured from the last detected PWA change.

7. The system of claim 1, wherein the wearable ring device comprises speakers and LED light indicators, optionally wherein the wearable device comprises input hardware to modify the duration and intensity of the vibration motors.

8. The system of claim 1, wherein the real-time feedback comprises tactile feedback, thermal feedback, or a combination thereof.

9. The system of claim 1, configured to operate in offline mode, with the one or more physiological data and real-time feedback provided without requiring internet connectivity.

10. The system of claim 1, wherein the one or more physiological data comprise blood flow, blood flow volume, blood flow volume change, blood pulse volume, breathing rate, heart rate, or a combination thereof.

11. The system of claim 1, configured to provide the real-time feedback to the first subject or second subject once changes in the PWA data indicate a PWA drop of 5%, 10%, 15%, 20%, 25%, 30%, 35%, 40% or more from an established PWA baseline.

12. The system of claim 1, comprising a machine learning algorithm to detect and classify PWA drop patterns over time.

13. A method for managing and/or treating one or more conditions or disorders in a first subject in need thereof, the method comprising attaching the system of claim 1 to the first subject.

14. The method of claim 13, wherein the one or more conditions or disorders are relatable to activities associated with the first subject's sympathetic nervous system.

15. The method of claim 13, wherein the one or more conditions or disorders comprises insomnia; anxiety; stress; epilepsy; burn out; attention deficit/hyperactivity disorder; sleep disorder/disturbance or effects thereof; or a combination thereof.

16. The method of claim 13, further comprising:

(i)(providing guided relaxation prompts comprising diaphragmatic breathing exercises, upon detection of significant sympathetic nervous system activity as indicated by a drop in PWA of 5%, 10%, 15%, 20%, 25%, 30%, 35%, 40% or more from an established PWA baseline; and/or (ii) logging and/or analyzing user data over time, including PWA fluctuations, frequency of alerts, and user engagement with relaxation prompts, and optionally generating reports to allow users to track and understand patterns related to stress and sleep disturbances.

17. The system of claim 1, wherein the user-actuated button is configured to allow a user to adjust feedback during user-signaled exertion.

18. The system of claim 1, configured to (i) automatically deactivate after a stable PWA period, or (ii) produce the haptic alert and a mobile-application-delivered diaphragmatic breathing relaxation (DBR) prompt.

19. The system of claim 1, configured for re-establishment of a subsequent baseline PWA value from PPG signal data from the subject triggered by subsequent button actuation.

* * * * *